United States Patent [19]

Lerch

[11] Patent Number: 5,474,744
[45] Date of Patent: Dec. 12, 1995

[54] AUTOMATIC PIPETTING DEVICE WITH CLEANING MECHANISM

[75] Inventor: Erich Lerch, Lucerne, Switzerland

[73] Assignee: Hoffmann-La Roche Inc., Nutley, N.J.

[21] Appl. No.: 327,535

[22] Filed: Oct. 21, 1994

[30] Foreign Application Priority Data

Oct. 28, 1993 [CH] Switzerland .................. 3253/93

[51] Int. Cl.⁶ ................ G01N 35/10; B08B 3/04
[52] U.S. Cl. ................ 422/100; 422/63; 422/81; 422/103; 436/43; 436/49; 436/150; 73/864.22; 134/169 R; 134/170
[58] Field of Search ................ 422/63, 64, 65, 422/67, 81, 100, 103; 436/43, 49, 54, 175, 180; 73/864.22; 134/169 R, 170

[56] References Cited

U.S. PATENT DOCUMENTS

| | | | |
|---|---|---|---|
| 3,266,322 | 8/1966 | Negersmith et al. | 73/864.22 |
| 3,911,749 | 10/1975 | Hendry | 73/864.22 |
| 3,912,456 | 10/1975 | Young | 422/64 |
| 4,318,885 | 3/1982 | Suzuki et al. | 422/68 |
| 4,457,184 | 7/1984 | Shiono | 73/864.11 |
| 4,516,437 | 5/1985 | Pedroso et al. | 73/864.22 |
| 4,635,665 | 1/1987 | Namba et al. | 134/167 R |
| 4,730,631 | 3/1988 | Schwartz | 134/155 |
| 4,820,497 | 4/1989 | Howell | 422/63 |
| 4,926,701 | 5/1990 | Tompkins | 73/864.15 |
| 4,948,563 | 8/1990 | Kanewske, III | 422/99 |
| 5,133,373 | 7/1992 | Hoffman et al. | 134/88 |
| 5,186,194 | 2/1993 | Kitajima | 134/154 |

FOREIGN PATENT DOCUMENTS

3302730  1/1982  Denmark.
0257353  8/1987  European Pat. Off..
0535612  9/1992  European Pat. Off..

OTHER PUBLICATIONS

Japanese Abstract vol. No. 6, No. 62 (P–111) (1982).
Japanese Abstract vol. No. 6, No. 229 (P–155) (1982).

*Primary Examiner*—James C. Housel
*Assistant Examiner*—Long V. Le
*Attorney, Agent, or Firm*—George M. Gould; George W. Johnston; Robert A. Silverman

[57] ABSTRACT

An automatic pipetting device comprising only one pipetting needle having a tip end and an open end. The device comprises a metering syringe having an outlet. The device also comprises a mechanism for cleaning the pipetting needle with a cleaning fluid when the pipetting needle is positioned in a cleaning position. The mechanism comprises a plunger pump, a second tube having a first end and a second end, a first valve, a second valve, and a third tube having a first end and a second end, the second end of the tubing immersed in a cleaning fluid. The second end of the first tube is in fluid communication with both the outlet of the metering syringe and the first valve. The first end of the second tube is in fluid communication with the first valve. The second end of the second tube is in fluid communication with both the plunger pump and the second valve. The first end of the third tube is in fluid communication with the second valve. The mechanism for cleaning the pipetting needle is operated to activate the plunger pump and for opening and closing the first valve and the second valve, so as to establish a predetermined pressure of cleaning fluid in the second tube while the first and second valves are closed and subsequently to force the cleaning fluid through the pipetting needle while the first valve is open and the second valve is closed.

10 Claims, 2 Drawing Sheets

AUTOMATIC PIPETTING DEVICE WITH CLEANING MECHANISM

BACKGROUND OF THE INVENTION

1. Field

The invention relates to an automatic pipetting device.

2. Background

The invention relates to an automatic pipetting device in which only one pipetting needle is available with its own appropriate metering and transport means for the pipetting needle, the pipetting needle being connected to a metering syringe by a first tube and a first T-connection.

In the area of automatic analysers, for example those used for performing chemical analyses clinically, automatic pipetting devices of the above kind are known which usually form part of such an analyser and which serve for metering and transferring liquid samples or specimens and reagents between various containers, for example, from a reagent container or sample or specimen container into a measuring dish where a mixture of sample or specimen and reagent is formed and is analysed in the analyser. Known pipetting devices of this kind comprise a transport means which moves the pipetting needle into a number of pipetting positions and, between the pipetting operations, into a cleaning position, where the pipetting needle is cleaned with a suitable liquid, so that each pipetting operation may be carried out with a clean pipetting needle free from residues of any previous pipetting operation.

In the case of larger analysers, two independent pipetting devices, for example, are provided each with its own appropriate metering and transport means for the pipetting needles. This enables either pipetting needle to be used alternately while the other pipetting needle is being cleaned. Since the cleaning of one of the pipetting needles and the use of the other pipetting needle for performing a pipetting operation take place simultaneously, the duration of the working cycle of the pipetting device is not lengthened by the interval for cleaning the pipetting needle, that is, the duration of the interval required for cleaning the pipetting needle does not affect the duration of the working cycle of the pipetting devices of the analyser and therefore has no effect on the duration of the analyser working cycle. The sample or specimen throughput, that is, the number of samples or specimens which can be examined with the analyser per unit of time, is therefore independent of the duration of the interval required for cleaning the pipetting needle.

In the case of smaller analysers, with the aim of minimum apparatus complexity, there is usually just one pipetting device available, that is, just one pipetting needle with its metering and transport means. One consequence of this simplification of the analyser is that the interval required for cleaning the pipetting needle must be integrated into the analyser working cycle. The latter thus becomes longer and sample or specimen throughput becomes reduced.

BRIEF SUMMARY OF THE INVENTION

An object of the invention is to provide a pipetting device in which only one pipetting needle is available of the type referred to hereinbefore, which requires the shortest possible interval for cleaning the pipetting needle, but which guarantees thorough cleaning thereof.

One aspect of the invention relates to a pipetting device in which only one pipetting needle is available of the type referred to hereinbefore, in which one arm of the first T-connection is connected to a cleaning means comprising the following components:

a) a plunger pump connected by a second T-connection, a second tube and a first valve to one arm of the first T-connection, b) a suction tube, which is immersed in a cleaning liquid contained in a container and which is connected to one arm of the second T-connection by a second valve, and c) a control means for controlling the first valve, the second valve and the plunger pump.

Another aspect of the invention relates to a pipetting device in which only one pipetting needle is available of the type referred to hereinafter, in which one arm of the first T-connection is connected to a cleaning means comprising the following components:

a) a plunger pump connected by a second T-connection, a second tube and a valve to one arm of the first T-connection, b) a suction tube, which is immersed in a cleaning liquid contained in a container and which is connected to one arm of the second T-connection by a non-return valve, and c) a control means for controlling the valve and the plunger pump.

The main advantage of the pipetting device according to the invention over prior art pipetting devices is that thorough cleaning of the pipetting needle is achieved in a relatively short time and with minimum expense in terms of materials.

Exemplified embodiments of the invention will be described hereinafter with reference to the accompanying drawings in which:

DESCRIPTION OF THE PREFERRED EMBODIMENTS

Figure 1:
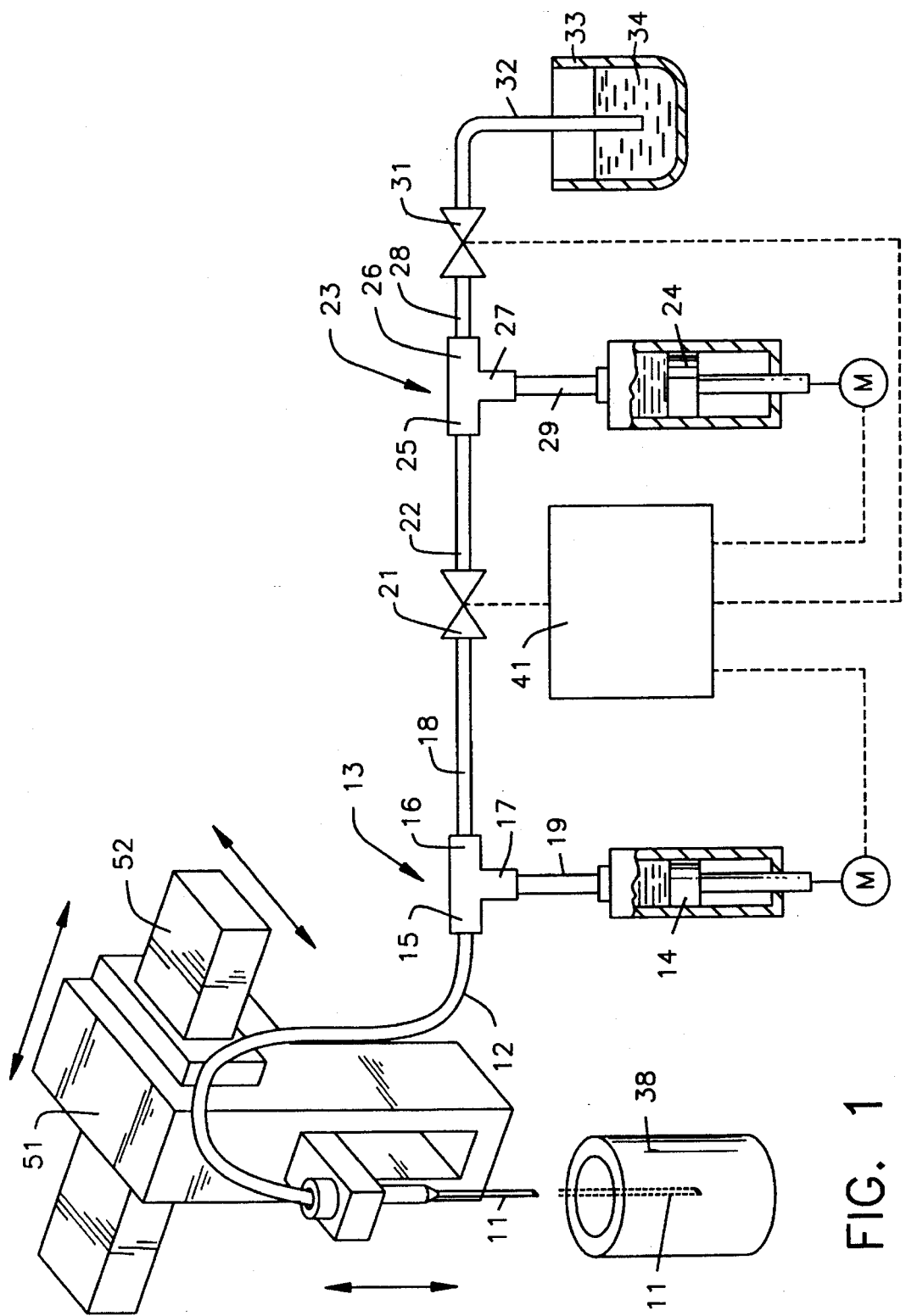
FIG. 1 is a diagram showing a pipetting device according to the invention.

An automatic pipetting device according to the invention comprises only one pipetting needle having a tip end and an open end. A transport means is secured to the pipetting needle for moving the pipetting needle to a plurality of pipetting positions and to a cleaning position. The device also comprises a metering syringe having an outlet. The first end of a first tube having a first end and a second end is secured to the open end of the pipetting needle. The device also comprises means for cleaning the pipetting needle with a cleaning fluid when the pipetting needle is positioned in the cleaning position.

In a first preferred embodiment, the means for cleaning the pipetting needle with a cleaning fluid comprises a plunger pump, a second tube having a first end and a second end, a first valve, a second valve, and a third tube having a first end and a second end, the second end of the third tube immersed in a cleaning fluid. The second end of the first tube is in fluid communication with both the outlet of the metering syringe and the first valve. The first end of the second tube is in fluid communication with the first valve. The second end of the second tube is in fluid communication with both the plunger pump and the second valve. The first end of the third tube is in fluid communication with the second valve. The means for cleaning the pipetting needle with a cleaning fluid also comprises means for activating the plunger pump and for opening and closing the first valve and the second valve, so as to establish a predetermined pressure of cleaning fluid in the second tube while the first and second valves are closed and subsequently to force the cleaning fluid through the pipetting needle while the first valve is open and the second valve is closed.

In another preferred embodiment, the means for cleaning the pipetting needle with a cleaning fluid comprises a plunger pump, a second tube having a first end and a second end, a valve, a non-return valve, and a third tube having a first end and a second end, the second end of the third tube immersed in a cleaning fluid. The second end of the first tube is in fluid communication with both the outlet of the metering syringe and the first valve. The first end of the second tube is in fluid communication with the valve. The second end of the second tube is in fluid communication with both the plunger pump and the non-return valve. The first end of the third tube is in fluid communication with the non-return valve. The means for cleaning the pipetting needle with a cleaning fluid also comprises means for activating the plunger pump and for opening and closing the valve, so as to establish a predetermined pressure of cleaning fluid in the second tube, thereby closing the non-return valve, while the valve is closed and subsequently to force the cleaning fluid through the pipetting needle while the first valve is open.

Preferably, a first T-connection communicates the second end of the first tube with both the outlet of the metering syringe and the first valve and a second T-connection communicates the second end of the second tube with both the plunger pump and the first end of the third tube.

The invention also relates to a method of cleaning a pipetting needle of the above pipetting devices. The method comprises moving the pipetting needle to the cleaning position, drawing cleaning liquid into the suction tube and providing a turbulent flow of cleaning liquid through the pipetting needle.

As shown in FIG. 1, a pipetting device according to the invention comprises only one metal pipetting needle 11 connected to a high-precision metering syringe 14 by a first tube 12, e.g. a Teflon tube, and a first T-connection 13, the first tube 12 being connected to one arm 15 of the T-connection 13 and the outlet of the metering syringe 14 being connected by a tube 19 to one arm 17 of the T-connection 13.

The metering syringe 14 has a metal cylinder and a plastic plunger with a rubber seal, its spindle being driven by a stepping motor.

In operation, the metering syringe 14 and a part of the tube 12 connected thereto contain a volume of water as a pressure transmission medium. The volume of a liquid for pipetting with the pipetting needle, for example, a reagent from a reagent container or sample or specimen from a sample container, is received in the interior of the pipetting needle 11 and, if necessary, partly also in an adjoining part of the tube 12. The liquid for pipetting is separated from the water in the tube 12 by an air bubble.

The pipetting device according to the invention comprises a transport means for the pipetting needle. The transport means comprises a bar 52, movable in the direction of the arrow by a drive (not shown), and a transport carriage 51 for the pipetting needle 11. Carriage 51 is movable along the bar 52 in the direction of the arrow by means of a drive (not shown). The carriage 51 contains a drive (not shown) by means of which the pipetting needle 11 is movable in the direction of the arrow. The above-described transport means enables the pipetting needle to be moved in three directions at right angles to one another so that it can be brought into a number of pipetting positions and also into a cleaning position.

In the cleaning position, cleaning liquid is pumped through the pipetting needle 11. The cleaning liquid which thereby emerges from the pipetting needle is received by a container 38. During the cleaning operation the pipetting needle 11 has the position shown in broken lines in FIG. 1 with respect to the container 38.

One arm 16 of the first T-correction 13 is connected to a cleaning device comprising the following components:

a) a plunger pump 24 connected to the arm 16 of the first T-connection 13 by a second T-connection 23, a second tube 22, a first valve 21 and a tube 18, the second tube 22 being connected to one arm 15 of the T-connection 23 and the outlet of the plunger pump 24 being connected to one arm 27 of the T-connection 23 by a tube 29, b) a suction tube 32 immersed in a cleaning liquid 34 contained in a container 33 and connected via a second valve 31 and a tube 28 to one arm 26 of the second T-connection 23, and c) a control device 41 for controlling the first valve 21, the second valve 31 and the plunger pump 24.

In a preferred embodiment, the control device is arranged such that it can control the first valve 21, the second valve 31 and the plunger pump 24 in such a manner that the following cycle takes place to perform a cleaning operation on the pipetting needle 11.

During a first interval, in which the second valve 31 is kept open and the first valve 21 is kept closed, cleaning liquid is sucked from the container 33 by the plunger pump 24. The first interval lasts about 7.8 seconds.

During a subsequent second interval, in which the second valve 31 and the first valve 21 are kept closed, the pressure in the tubes 22, 28, 29 is raised by the plunger pump 24. The second interval lasts about 0.2 seconds.

During a subsequent third interval, in which the first valve 21 is kept open and the second valve 31 kept closed, the pressure in the tubes 22, 28, 29 is kept substantially constant by the plunger pump 24, part of the cleaning liquid contained in the second tube 22 flowing out through the first tube 12 and the pipetting needle 11. The third interval lasts about 2 seconds.

The plunger pump 24 has a metal cylinder and a plastic plunger with a rubber seal, its spindle being driven by a stepping motor.

The plunger pump 24 serves to form a pressure in the tubes 22, 28, 29 during the above-mentioned second interval, the pressure being such that in the above-mentioned third interval the flow of cleaning liquid through the pipetting needle is a turbulent flow. This type of flow permits thorough cleaning of the interior of the pipetting needle in a very short time.

The flow of cleaning liquid through the first tube 12 should preferably also be turbulent, but within the scope of the invention it is sufficient for it to be a defined flow, which may be turbulent or laminar.

In order to achieve these flow conditions, all the participating components must have suitable dimensions. The dimensions of the pipetting needle 11 and of the tube 12 connected thereto will depend on the required accuracy of the volumes for pipetting within the range of volumes of the liquids for pipetting. This range may, for example, comprise small volumes, e.g. between 2 and 50 microliters for specimens, and larger volumes of up to about 200 microliters for reagents. It has been found that for this volume range the pipetting needle preferably should have an inside diameter of about 0.4 mm and the tube 12 preferably should have an inside diameter of about 0.8 mm in order to achieve the required accuracy of the pipetted volumes. The minimum length of the tube 12 is determined substantially by the maximum volume for pipetting. In the present exemplified embodiment the pipetting needle 11 has an inside diameter of 0.4 mm and a length of 115 mm; the tube 12 has an inside diameter of 0.8 mm and a length of 500 mm.

The other tubes in FIG. 1 have inside diameters of 1.6 and 3 mm.

Experiments have shown that with the above dimensions of the pipetting needle 11 and of the various tubes a flow of 2.5 milliliters of cleaning liquid within 2 seconds through the pipetting needle 11 is required to give a good cleaning effect of the interior of the pipetting needle 11 and of the tube 12.

In the cleaning operation the hydraulic resistance of the pipetting needle 11 and of the tube 12 produces practically the entire pressure loss while the pressure loss caused by the other components is practically negligible.

In order to produce the required turbulent flow in the pipetting needle 11 during the cleaning operation, it is necessary, under the above conditions, to generate a pressure about 6 bar in the tubes 22, 28, 29 in the above-mentioned second and third intervals by means of the plunger pump 24. In a preferred embodiment, each of the tubes 22, 28, 29 consists of a rigid material, i.e. a material which is practically non-deformable by the pressure of 6 bars, e.g. polyethylene. The choice of such a material for the tubes 22, 28, 29 ensures that the required pressure of about 6 bar and hence the required action of the cleaning means is maintained for a relatively long period.

Before the beginning of each cleaning operation all the tubes in FIG. 1 and also the pipetting needle 11 are vented by filling with cleaning liquid from the container 38. The valves 21, 31 and the plunger pump 24 are suitably controlled by the control means 41 for this venting operation as well. Only after the venting operation do the above three intervals in the cleaning operation take place.

After each cleaning operation, the valve 21 is closed in a fourth interval and the valve 31 opened in order to allow the pressure in the tube system 22, 28, 29 to drop to atmospheric pressure and take in fresh cleaning liquid 34. In this way the apparatus is prepared for the next cleaning cycle.

Figure 2:
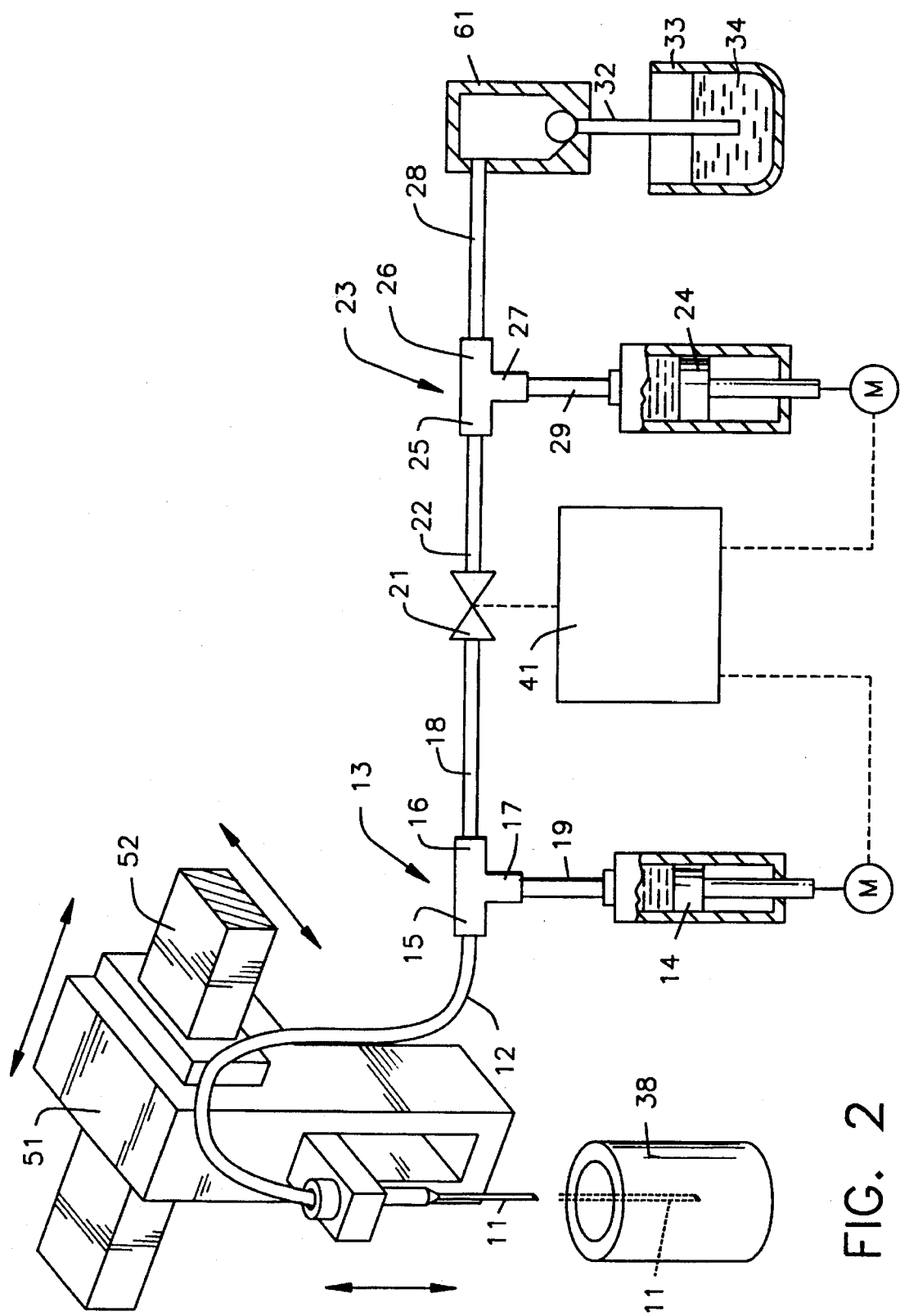
FIG. 2 is a preferred variant of the pipetting device according to FIG. 1.

FIG. 2 shows a preferred variant of the pipetting device according to FIG. 1. In the variant according to FIG. 2, a non-return valve 61 is used instead of the valve 31 in FIG. 1. The non-return valve 61 requires no control by the control means 41. If the plunger pump 24 produces a vacuum in the line 28, the non-return valve 61 is thus opened or kept open. When the plunger pump 24 produces a positive pressure in the line 28, the non-return valve 61 is thus closed or kept closed.

In the variant according to FIG. 2, the control means 41 is so arranged as to control the valve 21 and the plunger pump 24 in such manner that the following cycle takes place for performing a cleaning operation on the pipetting needle.

During a first interval, in which the valve 21 is kept closed and cleaning liquid is drawn in from the container 33 by the plunger pump 24, the non-return valve 61 is kept open by the negative pressure produced as a result, during a subsequent second interval, in which the valve 21 is kept closed and the pressure in the tubes 22, 28, 29 is raised by the plunger pump 24, the non-return valve 61 is kept closed by the positive pressure produced as a result, during a subsequent third interval, in which the valve 21 is kept open and the non-return valve 61 remains closed by the positive pressure, the pressure in the tubes 22, 28, 29 is kept approximately constant by the plunger pump 24, part of the cleaning liquid contained in the second tube 22 flowing out through the first tube 12 and the pipetting needle 11.

The construction and operation of the embodiment according to FIG. 2 is otherwise identical to or similar to that described above for the embodiment according to FIG. 1.

In both the embodiments described above, the control means 41 suitably controls both the stepping motor of the plunger pump 24 and the stepping motor of the metering syringe 14. For the above-described cleaning operation, the control of the plunger pump 24 by the control means 41 is important. The control of the stepping motor for the metering syringe 14 by the control means 41, on the other hand, is important for the metering operation which takes place outside the time of the cleaning operation.

While the invention has been described in conjunction with certain embodiments, it is understood that various modifications and changes may be made without departing from the spirit and scope of the invention.

I claim:

1. A pipetting device comprising:
   a) only one pipetting needle having a tip end and an open end;
   b) a transport means secured to the pipetting needle for moving the pipetting needle to a plurality of pipetting positions and to a cleaning position;
   c) a metering syringe having an outlet;
   d) a first tube having a first end and a second end, the first end of the first robe secured to the open end of the pipetting needle; and
   e) means for cleaning the pipetting needle with a cleaning fluid when the pipetting needle is positioned in the cleaning position, said cleaning means comprising:
      i) a plunger pump;
      ii) a second tube having a first end and a second end;
      iii) a first valve;
      iv) a second valve;
      v) a third tube having a first end and a second end, the second end of the third tube immersed in said cleaning fluid;
   wherein,
      1) the second end of the first tube is in fluid communication with both the outlet of the metering syringe and the first valve;
      2) the first end of the second tube is in fluid communication with the first valve;
      3) the second end of the second tube is in fluid communication with both the plunger pump and the second valve; and
      4) the first end of the third tube is in fluid communication with the second valve; and
      vi) control means for activating the plunger pump and for opening and closing the first valve and the second valve, so as to establish a predetermined pressure of cleaning fluid in the second tube while the first and second valves are dosed and subsequently to force the cleaning fluid through the pipetting needle while the first valve is open and the second valve is closed.

2. A pipetting device according to claim 1, wherein a first T-connection communicates the second end of the first tube with both the outlet of the metering syringe and the first valve and a second T-connection communicates the second end of the second tube with both the plunger pump and the first end of the third tube.

3. A pipetting device according to claim 2, wherein the second tube is made of a rigid material.

4. A pipetting device according to claim 3, wherein the second tube is made of polyethylene.

5. A pipetting device according to claim 2, wherein the pipetting needle has an inside diameter of about 0.4 mm and the first tube has an inside diameter of about 0.8 mm.

6. A pipetting device comprising:
  a) only one pipetting needle having a tip end and an open end;
  b) a transport means secured to the pipetting needle for moving the pipetting needle to a plurality of pipetting positions and to a cleaning position;
  c) a metering syringe having an outlet;
  d) a first tube having a first end and a second end, the first end of the first tube secured to the open end of the pipetting needle; and
  e) means for cleaning the pipetting needle with a cleaning fluid when the pipetting needle is positioned in the cleaning position, said cleaning means comprising:
    i) a plunger pump;
    ii) a second tube having a first end and a second end;
    iii) a valve;
    iv) a non-return valve;
    v) a third tube having a first end and a second end, the second end of the third tube immersed in said cleaning fluid;
  wherein,
    1) the second end of the first tube is in fluid communication with both the outlet of the metering syringe and the first valve;
    2) the first end of the second tube is in fluid communication with the valve;
    3) the second end of the second tube is in fluid communication with both the plunger pump and the non-return valve; and
    4) the first end of the third tube is in fluid communication with the non-return valve; and
  vi) control means for activating the plunger pump and for opening and closing the valve, so as to establish a predetermined pressure of the cleaning fluid in the second tube while the valve is closed, thereby dosing the non-return valve, and subsequently to force the cleaning fluid through the pipetting needle while the first valve is open.

7. A pipetting device according to claim 6, wherein a first T-connection communicates the second end of the first tube with both the outlet of the metering syringe and the first valve and a second T-connection communicates the second end of the second tube with both the plunger pump and the first end of the third tube.

8. A pipetting device according to claim 7, wherein the second tube is made of a rigid material.

9. A pipetting device according to claim 8, wherein the second tube is made of polyethylene.

10. A pipetting device according to claim 7, wherein the pipetting needle has an inside diameter of about 0.4 mm and the first tube has an inside diameter of about 0.8 mm.

* * * * *

UNITED STATES PATENT AND TRADEMARK OFFICE
CERTIFICATE OF CORRECTION

PATENT NO.   : 5,474,744                                Page 1 of 2
DATED        : December 12, 1995
INVENTOR(S)  : Erich Lerch It is certified that error appears in the above-indentified patent and that said Letters Patent is hereby corrected as shown below:

IN THE CLAIMS

Claim 1, Column 6, line 36: "robe" should read -- tube-- .

Claim 1, Column 6, lines 39-40: "the cleaning position, said cleaning means comprising:" should read -- said cleaning position, the means comprising: -- .

Claim 1, Column 6, line 63: "dosed" should read -- closed-- .

UNITED STATES PATENT AND TRADEMARK OFFICE
CERTIFICATE OF CORRECTION

PATENT NO. : 5,474,744
DATED : December 12, 1995
INVENTOR(S) : Erich Lerch

It is certified that error appears in the above-indentified patent and that said Letters Patent is hereby corrected as shown below:

Claim 6, Column 7, lines 24-25: "the cleaning position, said cleaning means comprising:" should read --- said cleaning position, the means comprising: --- .

Signed and Sealed this

Ninth Day of July, 1996

Attest:

BRUCE LEHMAN

*Attesting Officer*  *Commissioner of Patents and Trademarks*